United States Patent [19]
Inamatsu et al.

[11] Patent Number: 5,851,831
[45] Date of Patent: Dec. 22, 1998

[54] METHOD FOR LONG TERM SUBCULTURE OF DERMAL PAPILLA CELLS

[75] Inventors: Mutsumi Inamatsu; Takashi Matsuzaki; Katsutoshi Yoshizato, all of Hiroshima, Japan

[73] Assignee: Research Development Corporation of Japan, Japan

[21] Appl. No.: 419,708

[22] Filed: Apr. 11, 1995

[51] Int. Cl.⁶ .................................................. C12N 5/00
[52] U.S. Cl. .......................... 435/383; 435/373; 435/384
[58] Field of Search .............................. 435/240.1, 240.2, 435/240.3, 383, 384, 373

[56] References Cited

U.S. PATENT DOCUMENTS

| | | | |
|---|---|---|---|
| 4,919,664 | 4/1990 | Oliver et al. | 623/15 |
| 5,130,142 | 7/1992 | Wong et al. | 424/574 |
| 5,229,271 | 7/1993 | Philpott | 435/29 |
| 5,423,778 | 6/1995 | Eriksson et al. | 604/305 |

OTHER PUBLICATIONS

Jahoda, C.A.B. et al., "Supplement to The Journal of Investigative Dermatology," vol. 101(1), pp. 33S–38S, Jul. 1993.

Reynolds, A.J. et al., "The Journal of Investigative Dermatology," vol. 101(4), pp. 634–638, Oct. 1993.

Reynolds, A.J. et al., "Journal of Cell Science," vol. 98(part 1), pp. 75–83, Jan. 1991.

Watson, S.A.J. et al., British J. of Dermatology, vol. 131(6), pp. 827–835, 1994.

Heron, S.M. et al., British J. of Dermatology, vol. 122(2), p. 267, abstract, Feb. 1990.

Matsuzaki, T. et al., Zoological Science, vol. 11(Supplement), p. 61, abstract, Dec. 1994.

Reynolds, A.J. et al., J. of Dermatological Science, vol. 7(Supplement), pp. S84–S97, 1994.

*Primary Examiner*—Leon B. Lankford, Jr.
*Attorney, Agent, or Firm*—Wenderoth, Lind & Ponack, L.L.P.

[57] ABSTRACT

This invention provides a method for culturing dermal papilla cells with at least either of the mammalian epidermal cells from the sole or other portions of a mammal and the conditioned medium thereof, in order to permit long stable subculture of dermal papilla cells while keeping the original function thereof intact.

2 Claims, 11 Drawing Sheets

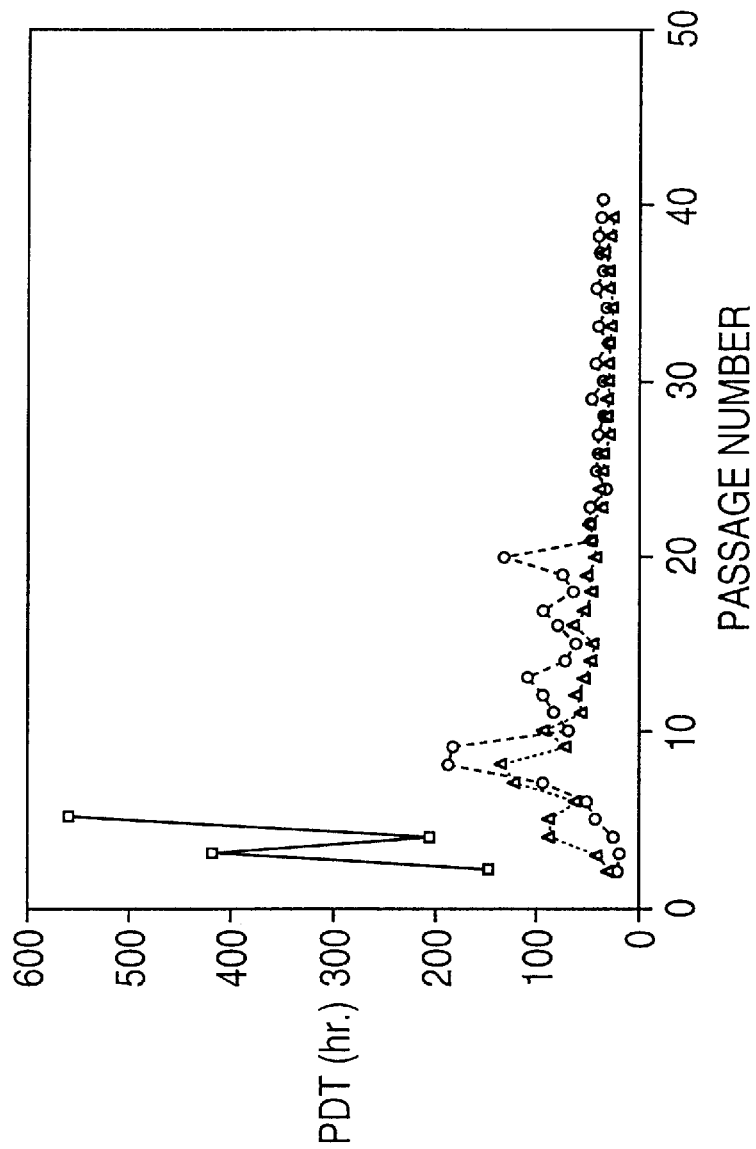

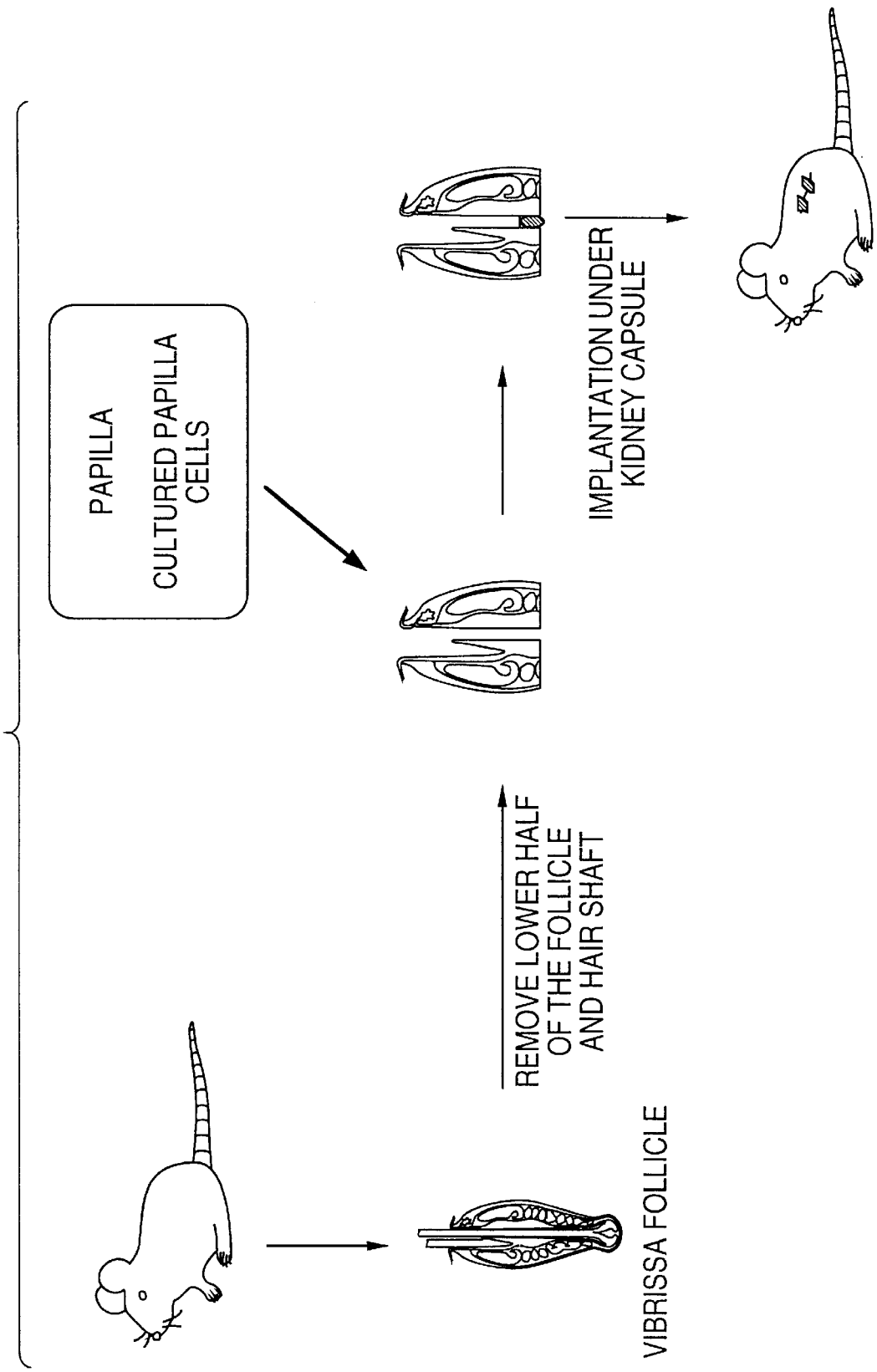

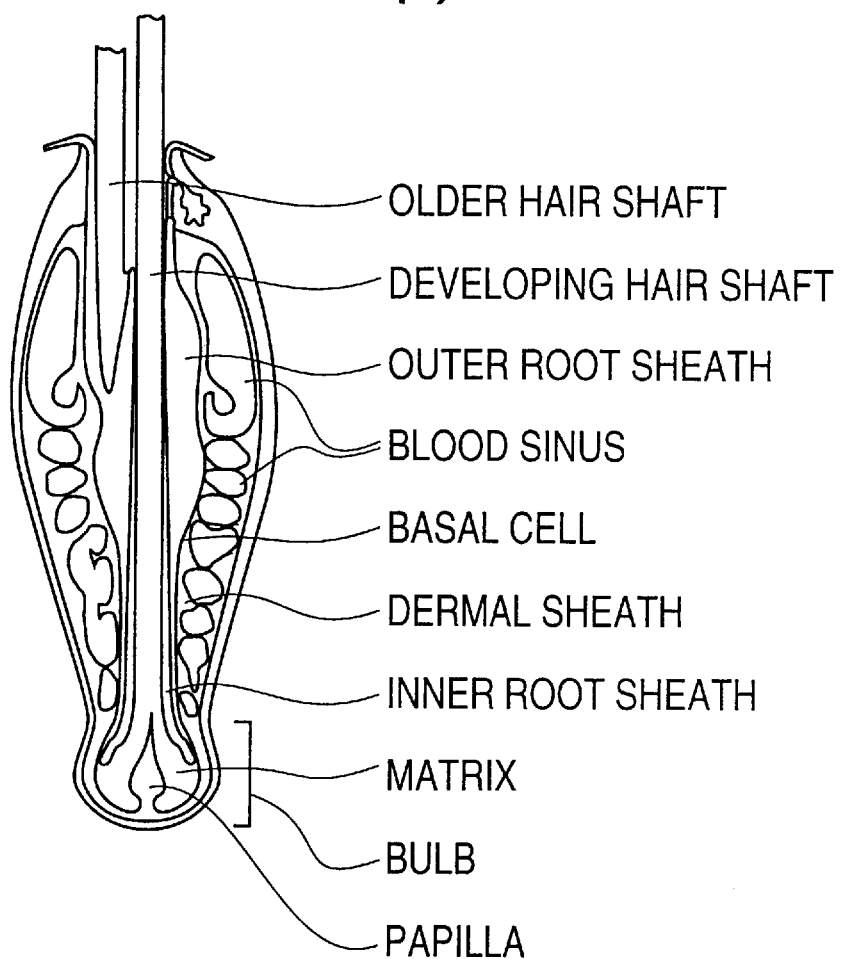

METHOD FOR LONG TERM SUBCULTURE OF DERMAL PAPILLA CELLS

FIELD OF THE INVENTION

The instant Invention relates to a method for long term subculture of dermal papilla cells of hair follicles. It relates more specifically to a new method for long term subculture of dermal papilla cells, useful for the artificial control of the differentiation and proliferation of hairs; this method facilitates Isolation and analysis of the differe ntiation/induction factors and growth factors of hair follicles and provides, in a limited period of time, large quantities of dermal papilla cells as transplantation materials.

PRIOR ART

It has been conventionally known that hairs are outgrowths of the skin and that interactions between the follicle epidermis and the underlying papillae result in the differentiation and proliferation of hair mattrix cells, thereby causing the hair shaft (so-called hair body) to grow.

Up to the present, studies have been made on the proliferation and growth of hair from various points of view. Oliver, for instance, cut in half a follicle (the portion of a hair embedded in the basal skin thereof) and filled papilla cells into the cut edge thereof, thereby showing that a follicle was reproduced. Based on this finding, he inferred that papilla cells play a vital role in the differentiation and proliferation of follicle (J. Embryol, Exp. Morph., 18:43-, '67)- From this, it can be presumed that papilla cells secrete the dif ferentiation/induction factors and growth factors.

Although these factors are considered of great importance in the artificial control of the differentiation and proliferation of hairs, the true nature thereof is yet to be elucidated.

Under these circumstances, in order to investigate and analyze these factors or make use of papilla cells as biotransplantation materials, a great deal of papilla cells must be available. Such cells in the follicles are limited in number, and hence there Is no alternative but to culture them to attain the above purpose. However, few successful cases of subculture of papilla cells have been reported; the rate at which cells were proliferated were not so fast as they should have been, and there was a limit to the number of subculture processes which could be carried out effectively: up to seven. The papilla cells which have undergone many subculture processes are filled into a halved follicle, but no new follicle is reproduced (Jahoda et al., Nature, 311:56-, '84). This indicates that those papilla cells have lost their original functions.

In order to overcome these limitations of the conventional technology, the present invention has the objective of providing a new method for long term subculture of dermal papilla cells, said method permitting long and stable subcultures of papilla cells without causing any loss of the functions thereof and serving as a means indispensable for the study of the differen tiation/induction factors and growth factors of the follicles and for the growth of hair and the development of papilla cells as biotransplantation materials.

SUMMARY OF THE INVENTION

The present invention provides a method for long term subculture of dermal papilla cells, which comprises culturing papilla cells with at least either of mammalian epidermal cells and a conditioned medium thereof.

The invention also provides a proliferation composition of papilla cells containing at least either of mammalian epidermal cells or a conditioned medium thereof, and a culture medium consisting of this composition.

BRIEF DESCRIPTION OF THE DRAWINGS

FIG. 1(a) being a culture without epidermal cells; FIG. (b) being a co-culture with epidermal cells. The scale in the drawings is 100 μm.

FIGS. 3(a)+3(d) being without a conditioned medium; FIGS. 3(b)+3(e) being with a conditioned medium CM5; and FIGS. 3(c)+3(f) being with CM8. The scale is 100 μm.

FIG. 4 shows the results of population doubling time (PDT) of subcultured papilla cells derived from rat vibrissa follicles: □—without conditioned medium; ▲—with CM5; and ○—with CM8.

FIG. 5(a) being a 5th-day state of the 5th passage with CM5; FIG. 5(b) being a 5th-day state of the 6th passage with CM8; FIG. 5(c) being a 7th-day state of the 23rd passage with CM5; and FIG. 5(d) being a 7th-day state of the 24th passage with CM8. The scale is 100μm.

FIG. 6 is a general diagram showing a method for a follicle reproduction test of papilla cells.

FIGS. 8(a)–8(c) show the results of immunostaining reproduced follicles: FIG. 8(a) showing staining with K1309 (matrix and inner root sheath specific antibody); FIG. 8(b) representing staining with K1310 (matrix and outer root sheath specific antibody); and FIG. 8(c) is a schematic of a rat vibrissa follicle.

DETAILED DESCRIPTION OF THE INVENTION

Figure 1A:
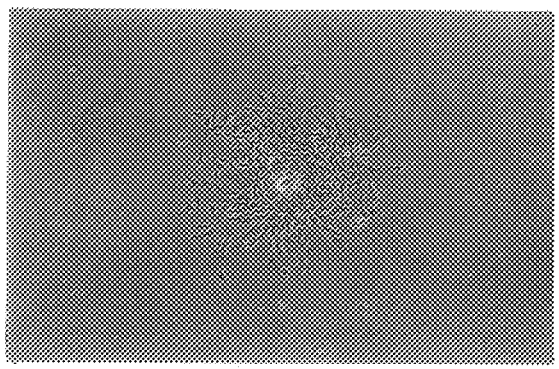
FIGS. 1(a) and 1(b) are drawings indicating the 8th-day state of the primary culture of papilla derived from rat vibrissa follicle.

Based on the new finding that dermal papilla cells are cultured with epidermal cells of the sole of a mammal, there will be a marked improvement on the proliferation thereof, the present invention is completed. This advantage can also be found in the conditioned medium of the epidermal cells. Using this conditioned medium, it becomes possible to subculture pure dermal papilla cells in a stable manner without any epidermal cells included, for more than 40 passages. When dermal papilla cells subcultured over more than 30 passages are filled into a half-cut follicle, it is observed that a new follicle is reproduced therein. Accordingly, this method makes it possible to culture dermal papilla cells for extended periods while keeping the original function thereof intact.

For this purpose, various kinds of epidermal cells of mammals, including rodents and Hominidae, can be applied. More preferably, the epidermal cells of a sole is employed in the present invention.

As described above, conventionally, the efficient outgrowth and proliferation of dermal papilla cells was not possible. This made it impossible or difficult to subculture dermal papilla cells for extended periods or while keeping the original function thereof (the ability to reproduce follicles) intact. The present invention has established a method for efficient long term subculture of dermal papilla cells by co-culturing the cells with sole epidermal cells or by adding a conditioned medium thereof. In addition, this culture method permits the subculture of dermal papilla cells without loss of the original function thereof (the ability to reproduce follicles). The technology made possible by the instant invention for culturing dermal papilla cells for extended periods while not causing any loss of the original functions thereof, facilitates the isolation and analysis of the differentiation/induction factors and growth factors of a follicle considered to be secreted by a dermal papilla cell, making It possible to provide dermal papilla cells as transplantation materials in large quantities and in a limited time. This is quite useful for the artificial control of the differentiation and proliferation of hairs.

Now, further detailed descriptions will be given with an example.

EXAMPLE

——Cell Culture——

1) Isolation of epidermal cells of rat's sole

A piece of skin is cut off from the sole of a rat and treated with dispase (Dispase, 1,000 U/ml, at 4° C., over night), separating the epidermis from the dermis The epidermis, thus obtained is then treated with trypsin (Trypsin, 0.25%, at 37° C., for 10 min.), and using the back side of forceps whose tops are bent, the cells are scraped off from the piece of epidermis treated. The cells are passed through a nylon mesh to remove lumps thereof.

2) Co-culture of sole epidermal cells and dermal papilla cells

The sole epidermal cells obtained in 1) above ($3.6 \times 10^5$ cells), and with dermal papillae isolated from vibrissa, are inoculated simultaneously into a 35 mm plastic petri dish containing Dulbecco's modified eagle medium (D-MEM) with 10% fetal calf serum. They are allowed to culture in an incubator of 5% $CO_2$ at 37° C.

3) Preparation of a conditioned medium of the sole epidermal cells

The sole epidermal cells obtained in 1) above are inoculated into a 10 cm plastic petri dish with a density of $4 \times 10^4$ cells/cm$^2$, and cultured in D-MEM with 10% fetal calf serum. The medium is collected and replaced with a new one on the fifth and eighth days, respectively, after the inoculation. The conditioned media obtained are filtrated for sterilization through a 0.22 µm membrane filter to give CM5 and CM8

4) Culture of dermal papilla cells of a rat vibrissa follicle

Dermal papillae are isolated from the follicle of the rat vibrissa follicle under a stereomicroscope. Eight dermal papillae are placed Into each of the 35 mm plastic petri dishes. They are cultured In three types of culture media: the one containing only D-MEM with 10% fetal calf serum, the one in which the foregoing CM5 or CM8 is mixed with the medium at 1:1. The media are replaced with new ones every three or four days. The cells outgrowing from the papillae become confluent and fill the dish, when they are subjected to a subculture process. Thereafter, the replacement of the media and the subculture processes are carried out every three or four days, and every other week, respectively.

——Cell Function Test——

1) Follicle reproduction test of papilla cells

The vibrissa follicle of a rat is isolated, and the lower half thereof is cut and removed. From the remaining upper half the shaft is removed, and into the opening created in the surface of the half-cut follicle after the shaft is removed, the cultured dermal papilla cells are peletted and filled. As a positive control, another follicle is prepared in which the papilla isolated from a follicle are filled into the opening in the cut surface. They are implanted under the kidney capsule of rat. The rat is subjected to laparotomy in the eighth week thereafter, with the kidney taken out and observed, as well as examined immunohistochemically.

——Immunohistochemistry——

1) Antibody staining of cultured cells

Cultured dermal papilla cells are cultured on a SUMILON cell desk. The cells, together with the cell desk, are fixed with acetone. Then, the cells are made to react with a 13xx antibody we prepared, causing it to develop color with a peroxidase-labeled secondary antibody and 3,3'-diaminobenzidine.

2) Antibody staining of the follicle subjected to implant under the kidney capsule The follicle collected after the laparotomy is cut into 5 µm frozen sections, and then is made to react with a 13xx antibody and peroxidase-labeled secondary antibody, causing it to develop color with 3,3'- diaminobenzidine.

——Results——

Figure 1B:
Figure 2:
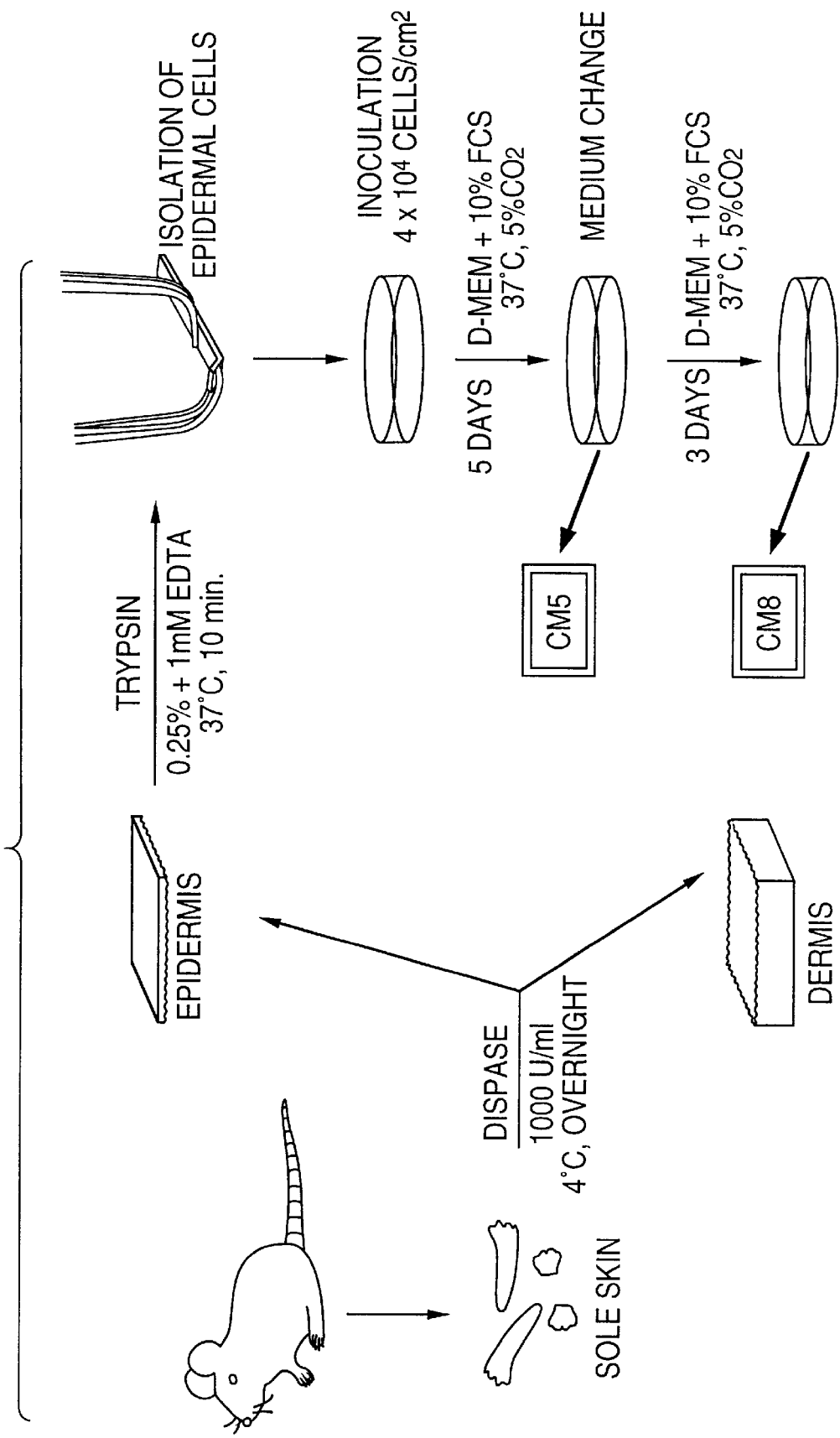
FIG. 2 is a process drawing showing a method for the preparation for conditioned medium of sole epidermal cells.
Figure 3A:
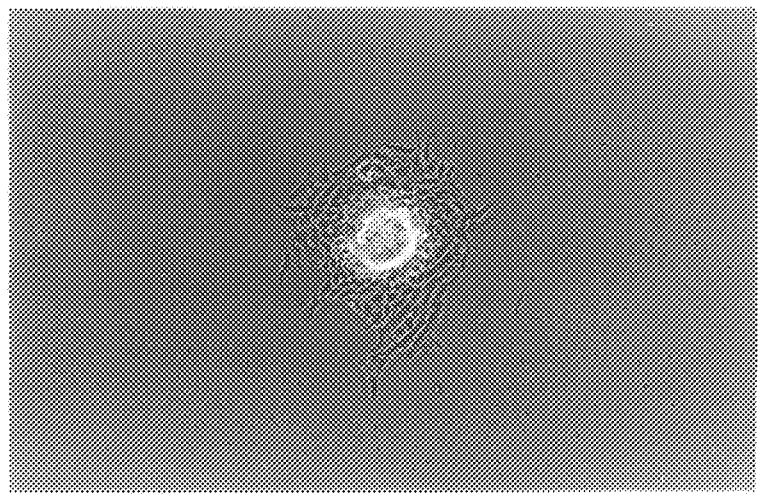
FIGS. 3(a)–3(f) are the drawings showing the 3rd-day state (FIGS. 3(a)–3(c)) and 6th-day state (FIGS. 3(d)–3(f)) of the culture of papilla derived from rat vibrissa follicle.
Figure 3B:
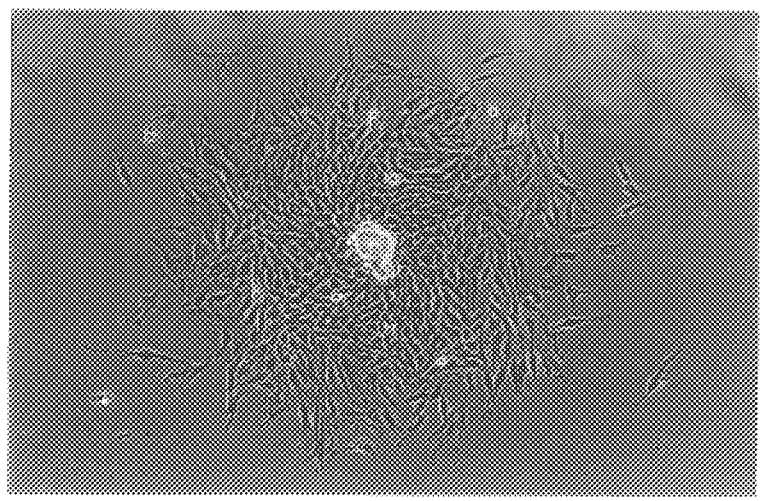
Figure 3C:
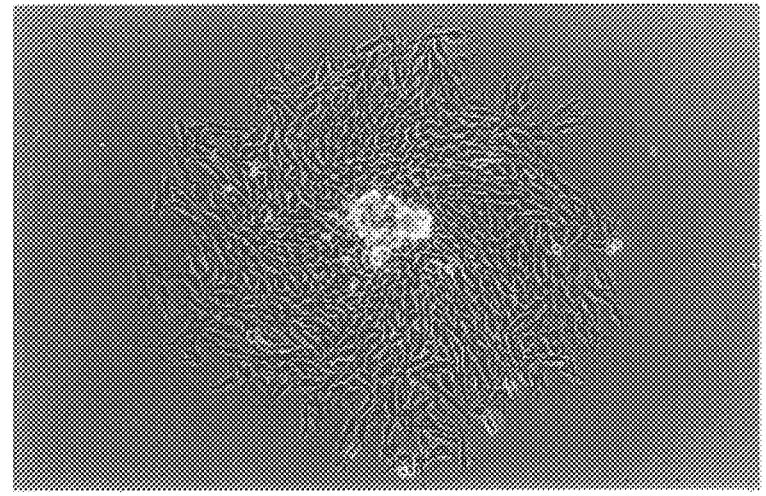
Figure 3D:
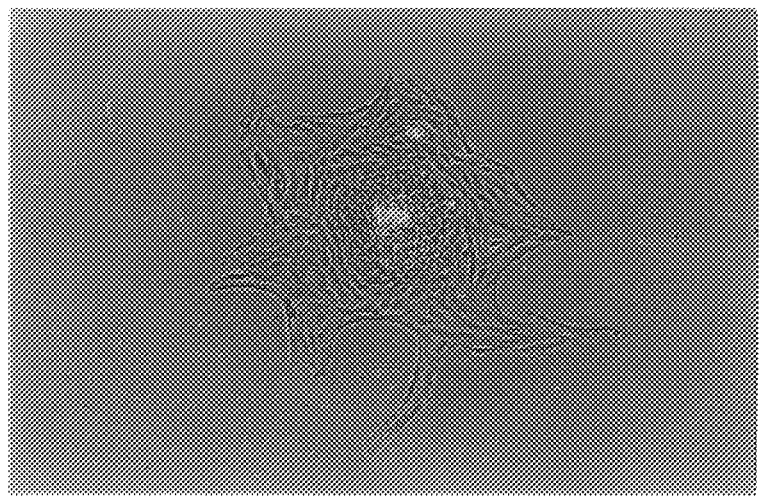
Figure 3E:
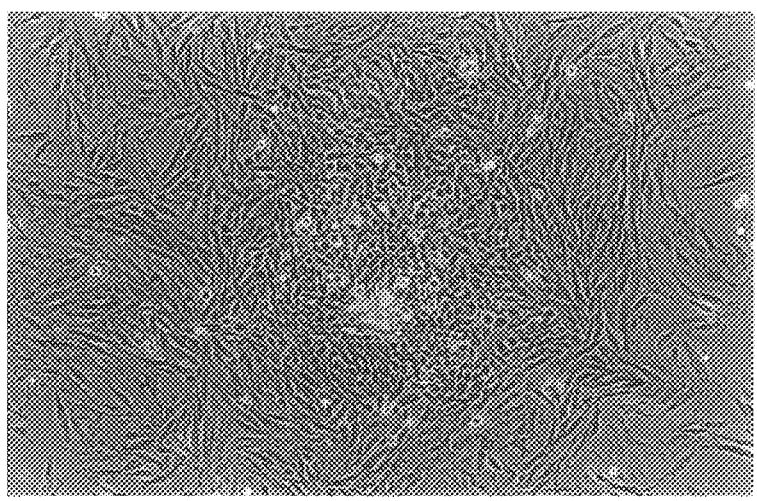
Figure 3F:
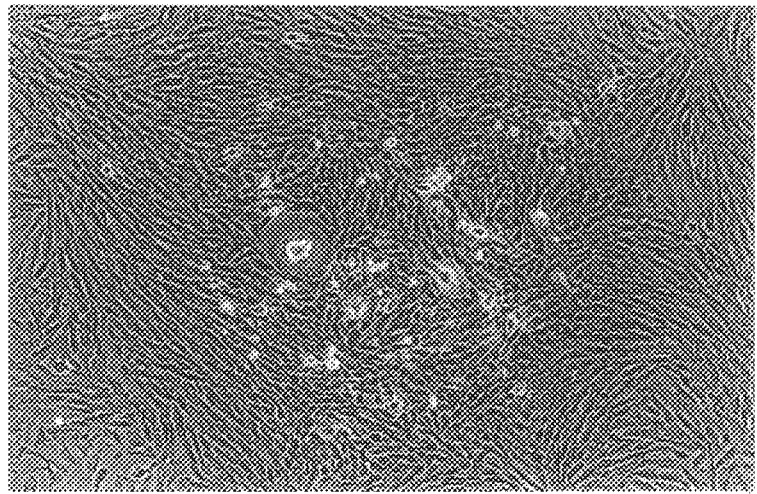

When the isolated dermal papillae are placed in a plastic petri dish for the primary culture, the cells began to outgrow from the dermal papillae adhered on the dish. As illustrated in FIG. 1, obviously enough, more favorable results were obtained in terms of both the state of the outgrowth of dermal papilla cells and the proliferation rate thereof, when they are co-cultured with the sole epidermal cells (FIG. 1:b) than when they are cultured alone (FIG. 1:a). Then, in order to determine whether the effect of the sole epidermal cells is derived from interactions between the cells or from the fluid factors secreted therefrom, the conditioned medium of the sole epidermal cells as indicated in FIG. 2 were added for the primary culture. The result was that better outgrowth and proliferation of the dermal papilla cells were observed when either conditioned medium CM5 or CM8 was added than the control, as shown In FIG. 3(a)–3(f). This indicates that some fluid factor(s) derived from sole epidermis activates the outgrowth and proliferation of dermal papilla cells.

Figure 5A:
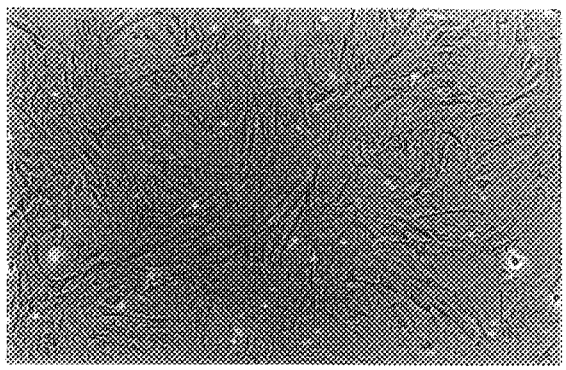
FIGS. 5(a)–5(d) are drawings indicating the state of subcultured papilla cells derived from rat vibrissa follicles with conditioned medium CM5 and CM8.
Figure 5B:
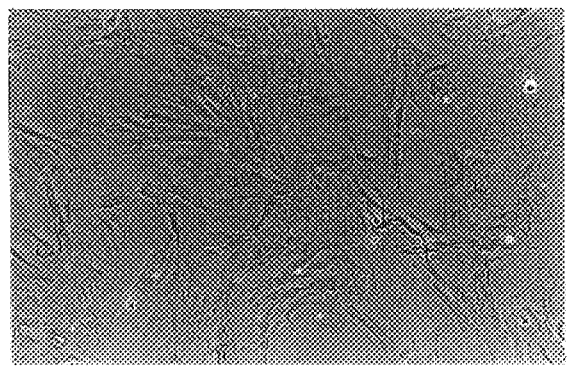
Figure 5C:
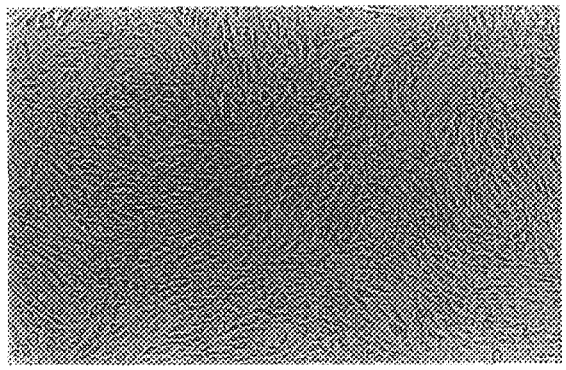
Figure 5D:
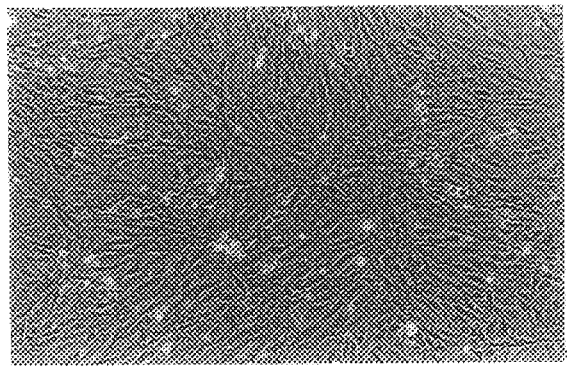

When the dermal papilla cells came to fill the petri dish, they were subjected to a subculture process. During the operation, the number of cells were counted to determine the population doubling time. As indicated in FIG. 4, after the 10th passage of subculture, the cells cultured with the conditioned medium added exhibited practically stable proliferation. On the other hand, for those cultured with nothing added, the proliferation rate gradually slowed down until at the fifth passage, virtually no increase was observed in the number of cells. Cultured with the conditioned medium added, the dermal capilla cells have been subjected to more than 40-passage subcultures, and a contact inhibition, one of the indicators of normality of cells, can be observed. As illustrated in FIG. 5(a)–(b), although the shapes of the cells have been different from those at the early stages of culture, they have come to be stable after the 10th-passage and subsequently. They were a little different between media containing CM5 and CM8.

Activation of outgrowth and proliferation of dermal papilla cells induced by the conditioned medium of the sole epidermal cells proved reproducible. The changes in cell shape after the subculture processes were found to be specific for each of the conditioned media.

Figure 7:
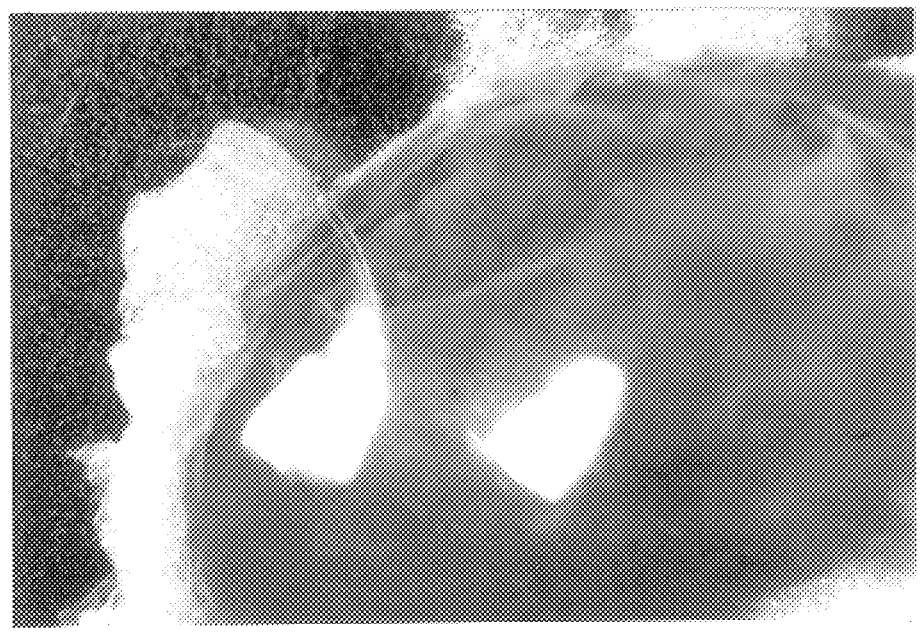
FIG. 7 indicates the state of 8 weeks after implantation of vibrissa follicles filled with cultured papilla cells (+CM5): The arrows shows the hair growth hair from reproduced follicles. The scale is 100 μm.
Figure 8A:
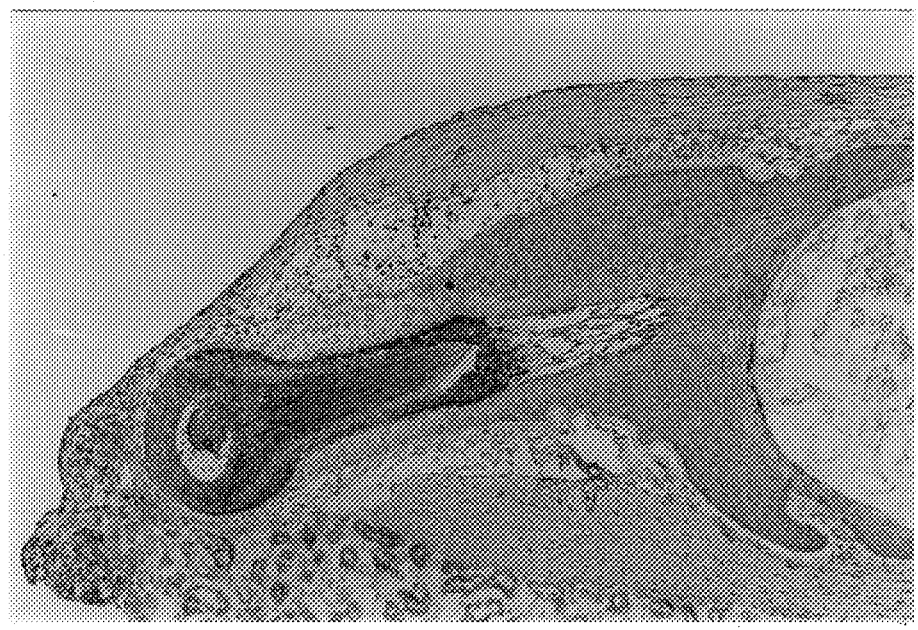
Figure 8B:
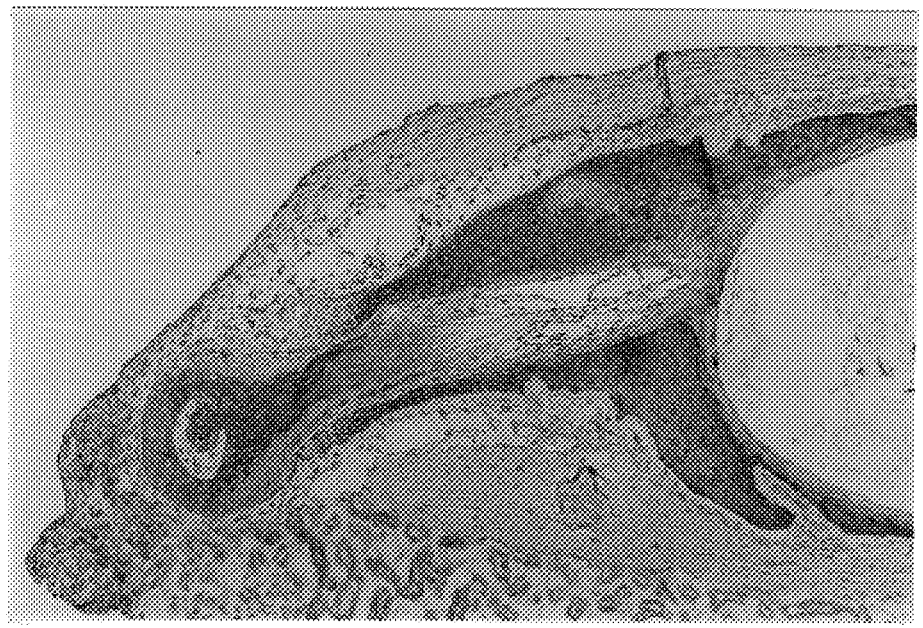

In order to study whether the dermal papilla cells cultured for extended periods using a conditioned medium, could retain the original function, as indicated in FIG. 6, a process of follicle reproduction was used for cell function tests. As a result, as illustrated in FIG. 7, even in the follicle filled with the dermal papilla cells subcultured over 30 passages, it was observed that a follicle was reproduced and the hair shaft grown. When various tissues of the follicles were stained with a monoclonal antibody (K13xx series), as illustrated in FIGS. 8(*a*)–8(*c*), the one reproduced showed its a histodifferentiation equivalent to a normal one.

We claim:

1. A method of long term cultivation of dermal papilla cells of a mammalian species, which comprises culturing and subculturing the dermal papilla cells in a cell culture medium which consists essentially of a medium conditioned by epidermal cells derived from said mammalian species, thereby proliferating the dermal papilla cells.

2. The method according to claim 1, wherein the epidermal cells are sole skin cells.

* * * * *

UNITED STATES PATENT AND TRADEMARK OFFICE
CERTIFICATE OF CORRECTION

PATENT NO.     : 5,851,831
DATED          : December 22, 1998
INVENTOR(S)    : Mutsumi Inamatsu et al.

It is certified that error appears in the above-identified patent and that said Letters Patent is hereby corrected as shown below:

<u>Title page,</u>
Item [73], please add -- Mutsumi Inamatsu of Hiroshima, Japan --

Signed and Sealed this

Fifth Day of November, 2002

Attest:

Attesting Officer

JAMES E. ROGAN
*Director of the United States Patent and Trademark Office*